US00PP27760P2

(12) United States Plant Patent
O'Connell

(10) Patent No.: US PP27,760 P2
(45) Date of Patent: Mar. 7, 2017

(54) ***KALANCHOE* PLANT NAMED 'BORDEAUX'**

(50) Latin Name: ***Kalanchoe* hybrid**
Varietal Denomination: Bordeaux

(71) Applicant: Renee O'Connell, Escondido, CA (US)

(72) Inventor: Renee O'Connell, Escondido, CA (US)

(73) Assignee: Altman Plants, Vista, CA (US)

( * ) Notice: Subject to any disclaimer, the term of this patent is extended or adjusted under 35 U.S.C. 154(b) by 0 days.

(21) Appl. No.: 14/756,715

(22) Filed: Oct. 1, 2015

(51) Int. Cl.
*A01H 5/02* (2006.01)

(52) U.S. Cl.
USPC ..... Plt./335

(58) Field of Classification Search
USPC ..... Plt./335, 339, 337
CPC ..... A01H 5/0266
See application file for complete search history.

*Primary Examiner* — Kent L Bell
(74) *Attorney, Agent, or Firm* — Cassandra Bright

(57) ABSTRACT

A new and distinct *Kalanchoe* cultivar named 'Bordeaux' is disclosed, characterized by attractive dusky red-burgundy foliage with attractive variable dentate leaf margins. The new cultivar freely branches, enabling increased and faster propagation. The new cultivar 'Bordeaux' exhibits robust and rapid growth. The freely branching characteristic exhibited by the new cultivar, in combination with the robust, moderately rapid growth of the new cultivar 'Bordeaux', results in attractive clustering plants at an early age, thereby enhancing production intervals. The new cultivar has proven landscape and full sun tolerant, qualities not displayed by many other comparable *Kalanchoes* known to the Inventor. The new variety is an *Kalanchoe*, part of the Crassulaceae complex that includes *Aeonium, Echeveria, Graptopetalum, Sedum* and others. *Kalanchoe* is a popular genus, typically produced for the floriculture industry, as well as for uses as container plants for the patio, or as landscape plants.

3 Drawing Sheets

Latin name of the genus and species: *Kalanchoe* hybrid.
Variety denomination: 'BORDEAUX'.

BACKGROUND OF THE INVENTION

The new cultivar is a product of a planned breeding program. The new variety originated from a cross pollination of the unpatented seed parent, *Kalanchoe* 'PR15' with the pollen parent an unpatented, proprietary *Kalanchoe* hybrid referred to as *Kalanchoe* 'PS02'. The cross pollination was made in February 2012 in Vista, Calif., at a commercial greenhouse. The new cultivar Bordeaux' was discovered by the inventor, Renee O'Connell in September, 2012 in Vista, Calif., at a commercial greenhouse.

Asexual reproduction of the new cultivar 'Bordeaux' was first performed in Vista, Calif., at a commercial greenhouse, by terminal vegetative cuttings in October 2012. *Kalanchoe* 'Bordeaux' has since produced multiple generations and has shown that the unique features of this cultivar are stable and reproduced true to type.

SUMMARY OF THE INVENTION

The cultivar 'Bordeaux' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'BORDEAUX'. These characteristics in combination distinguish 'BORDEAUX' as a new and distinct *Kalanchoe* cultivar:

1. *Kalanchoe* 'Bordeaux' displays unique, attractive dusky red-burgundy foliage.

2. *Kalanchoe* 'Bordeaux' exhibits robust and moderately fast growth, in combination with unique foliage coloration.
3. *Kalanchoe* 'Bordeaux' branches freely, quickly forming full canopies.
4. *Kalanchoe* 'Bordeaux' is easily and rapidly propagated due to quick rooting of cuttings, robust growth, and prolific branching.
5. *Kalanchoe* 'Bordeaux' produces leaves with variably dentate margins, and occasionally produces cristate stems.
6. *Kalanchoe* 'Bordeaux' has proven to be landscape and full sun tolerant.

PARENTAL COMPARISON

Plants of the new cultivar 'Bordeaux' are similar to the seed parent *Kalanchoe* 'PR15' in most horticultural characteristics. However, plants of the new cultivar 'Bordeaux' display early and profuse branching, not displayed by the seed parent *Kalanchoe* 'PR15'. The new cultivar 'Bordeaux' forms plants with full canopies with many branches, in contrast to the sparser canopy of *Kalanchoe* 'PR15'. In addition, the new cultivar 'Bordeaux' has an unusual and distinct red-burgundy foliage color that intensifies in full sun, as compared to the gray-green foliage with reddish tinges of the seed parent *Kalanchoe* 'PR15'. The new cultivar 'Bordeaux' exhibits faster and more robust growth than is exhibited by *Kalanchoe* 'PR15'.

Plants of the new cultivar 'Bordeaux' are similar to the pollen parent *Kalanchoe* 'PS02' in most horticultural characteristics. However, plants of the new cultivar 'Bordeaux' display early and profuse branching, whereas *Kalanchoe* 'PS02' produces scant branching. The new cultivar has attractive dusky red-burgundy foliage as compared to the reddish green foliage of *Kalanchoe* 'PS02'.

COMMERCIAL COMPARISON

The new cultivar 'Bordeaux' can be compared to the unnamed unpatented commercial variety of *Kalanchoe pumila*. Plants of the *Kalanchoe pumila* are similar to plants of the new cultivar 'Bordeaux' in most horticultural characteristics. However, the new cultivar 'Bordeaux' displays a red-burgundy foliage color that is not displayed by the *Kalanchoe pumila*. Additionally, the new cultivar exhibits more robust and rapid growth than does the *Kalanchoe pumila*. The new cultivar 'Bordeaux' has proven full sun tolerant in the landscape as compared to *Kalanchoe pumila*, which prefers shade. 'Bordeaux' displays resistance to powdery mildew, not displayed by the *Kalanchoe pumila.*

The new cultivar 'Bordeaux' can be compared to the unpatented commercial variety *Kalanchoe blossfeldiana*. Plants of the *Kalanchoe blossfeldiana* are similar to plants of the new cultivar 'Bordeaux' in most horticultural characteristics. However, the new cultivar 'Bordeaux' displays a red-burgundy foliage color that is not displayed by the *Kalanchoe blossfeldiana*. The new cultivar 'Bordeaux' grows more robustly and more rapidly than the *Kalanchoe blossfeldiana*. In addition, plants of the cultivar 'Bordeaux' are more resistant to the *Rhizoctonia* stem rot than the *Kalanchoe blossfeldiana*. Plants of the cultivar 'Bordeaux' have proven to be much more tolerant of full sun in the landscape than the *Kalanchoe blossfeldiana.*

BRIEF DESCRIPTION OF THE PHOTOGRAPHS

The accompanying photographs in FIG. 1 through FIG. 3 illustrate in full color typical plants of 'BORDEAUX' grown in a greenhouse in Vista, Calif. The photographs were taken using conventional techniques and equipment. While the colors in these photographs may display variances of color as compared to the living cultivar, due to LRV (light reflectance value), they are as accurate as possible using conventional photographic techniques. Colors in the photographs may appear to differ slightly from the color values cited in the botanical description, which accurately describe the colors of the new *Kalanchoe* plant. The following photographs depict plants grown under natural light conditions of 2500-4000 foot-candles. Temperatures ranged from −1° C. to 29° C. night and day. No artificial light, photoperiodic treatments or chemical treatments were given to the plants.

DETAILED BOTANICAL DESCRIPTION

Figure 1:
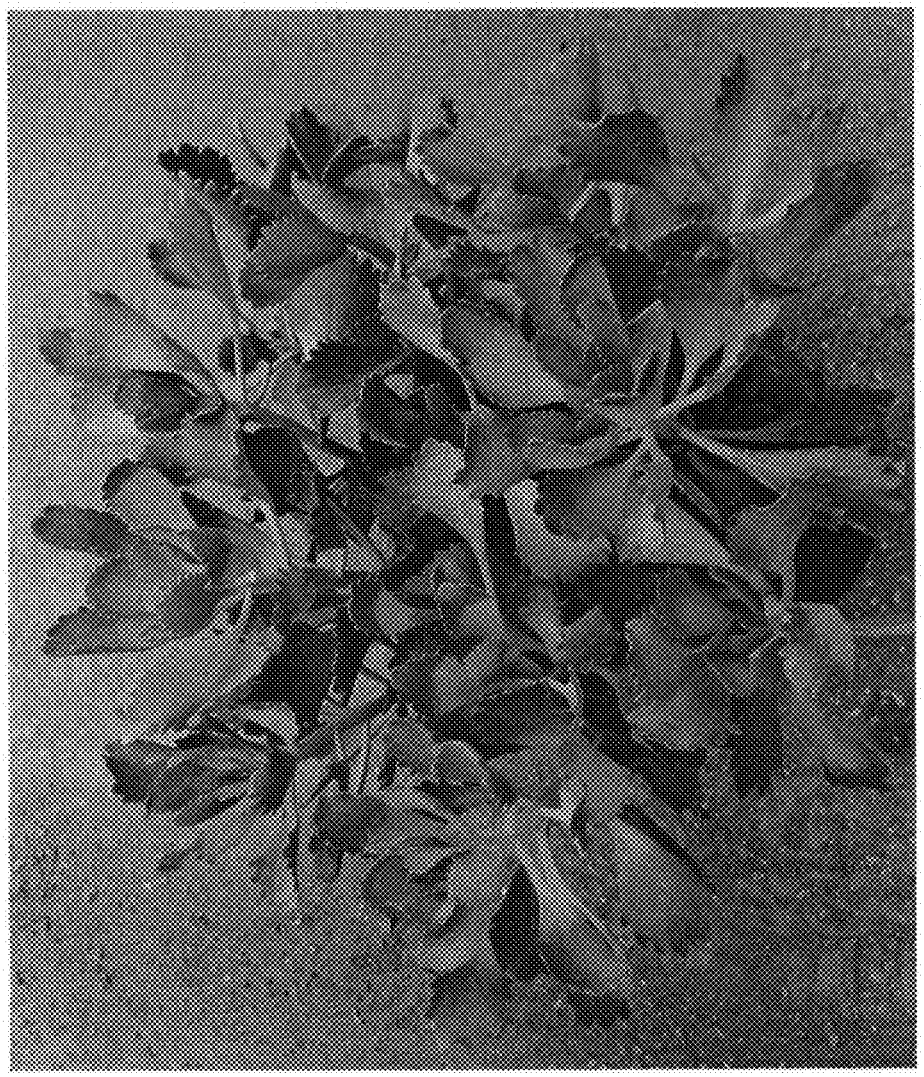
FIG. 1 illustrates in full color the side view of a typical plant of *Kalanchoe* 'Bordeaux' grown in full sun (approximately 9000 to 10000 foot candles) in Vista, Calif.
Figure 2:
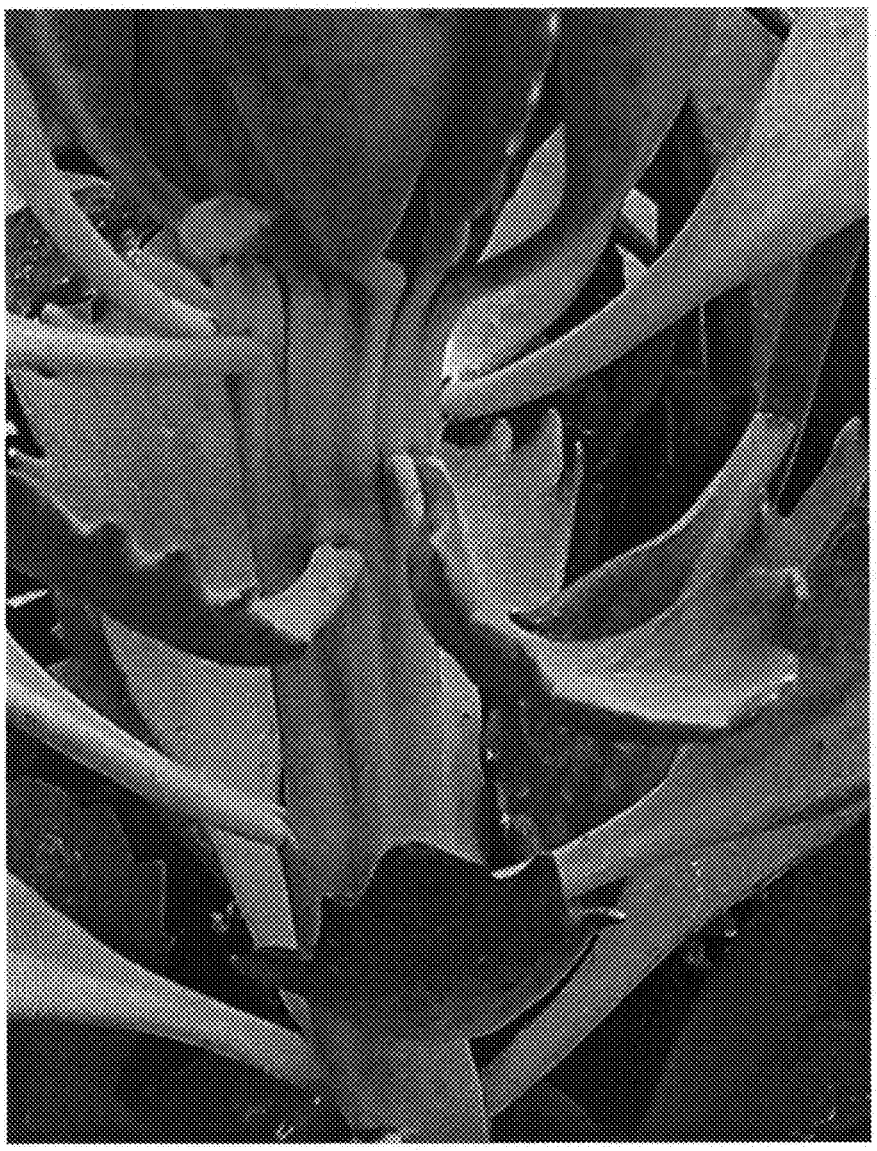
FIG. 2 illustrates in full color the occasional cristate stem that can be produced by *Kalanchoe* 'Bordeaux'.
Figure 3:
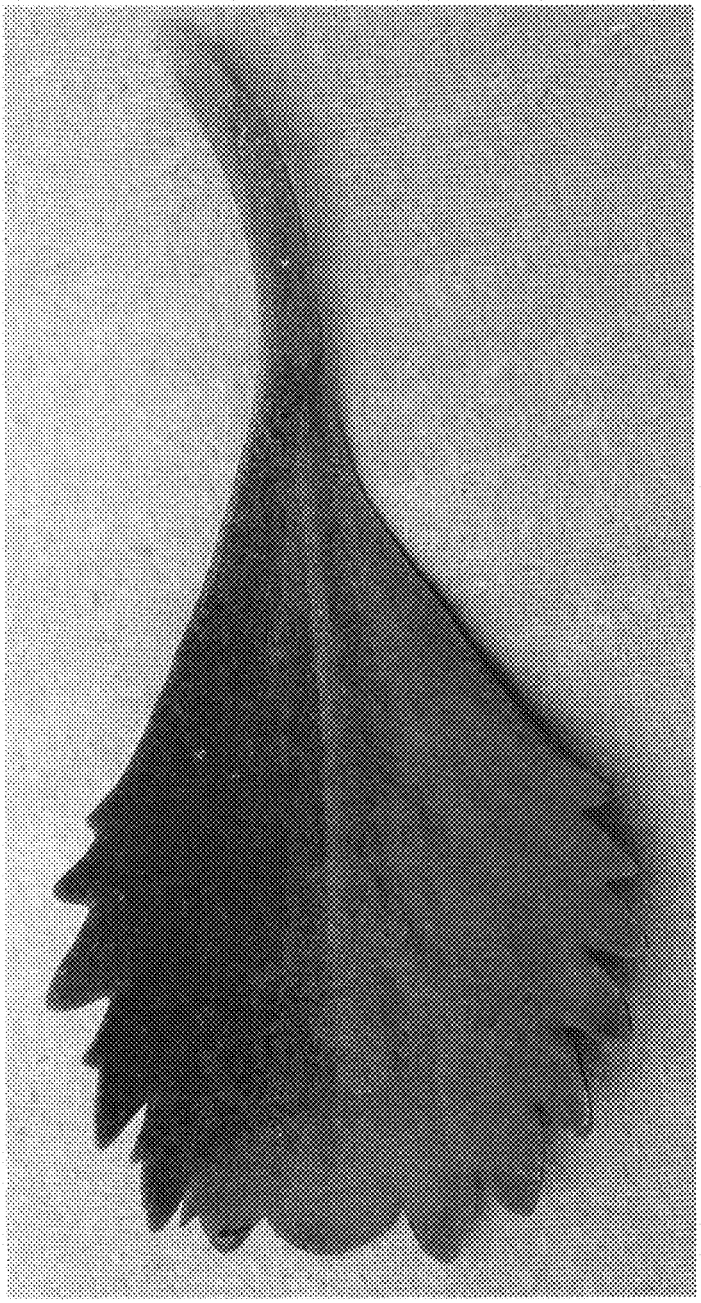
FIG. 3 illustrates in full color the variable dentate leaf margins of the new cultivar *Kalanchoe* 'Bordeaux'

In the following description, color references are made to the Pantone Process Color System Guide, Pantone CYMK, 2014, except where general terms of ordinary dictionary significance are used. The following observations and measurements describe 'Bordeaux' plants in a commercial greenhouse in Vista, Calif. Temperatures ranged from −1° C. to 29° C. night and day. No artificial light, photoperiodic treatments or chemical treatments were given to the plants. Natural light conditions were approximately 2500 to 4000 fc of light. Measurements and numerical values represent averages of typical plant types.

Botanical classification: *Kalanchoe* hybrid 'BORDEAUX'.

PROPAGATION

Type of propagation typically used: Terminal vegetative cuttings.

Time to initiate roots: About 10 days at approximately 24° C.

Root description: Fibrous.

PLANT

Age of plant described: Approximately 4 months from a cutting.

Container size of the plant described: 15 cm.

Growth habit: Upright branching sub-shrub.

Height: Approximately 25 cm to top of highest leaf. Approximately 33 cm. to top of highest inflorescence.

Plant spread: Approximately 37 cm. Plant comprised of 14 stems.

Growth rate: Moderately fast.

Branching characteristics: Freely branching from an early age; and apical pinching produces very full canopies.

FOLIAGE

Leaf:

*Arrangement.*—Irregular, opposite.

*Average length.*—Approximately 7 to 8 cm. Longest 9.5 cm.

*Average width.*—3.5 cm.

*Widest width.*—Approximately 4.5 cm.

*Width at base.*—0.4 cm.

*Shape of blade.*—Oblanceolate.

*Apex.*—Acute.

*Base.*—Rounded.

*Margin.*—Irregularly dentate.

*Texture of top surface.*—Glabrous.

*Texture of bottom surface.*—Glabrous.

*Quantity of leaves per plant.*—Approximately 125.

Color: The closest color for the foliage is S 323-1 Pantone, but the foliage is a darker shade of the color (no exact match exists on the color chart).

*Young foliage, upper side, near apex.*—Near S 323-1 Pantone.

*Young foliage, upper side, inward from apex.*—Near S 323-2 Pantone.

*Young foliage upper side, near base.*—Near S 306-6 Pantone, with an overlay of S 137-5 Pantone. S 163-1 Pantone is the closest in hue to the burgundy tint exhibited by 'Bordeaux', but the color chip is less saturated than the plant.

*Young foliage, upper side, basal margin.*—Near S 160-5 Pantone.

*Young foliage, under side, near apex.*—Near S 323-1 Pantone.

*Young foliage, under side, mid leaf.*—Near S 293-4 Pantone.

*Young foliage, under side, near apex.*—Near S 323-1 Pantone.

*Young foliage, under side, mid leaf.*—Near S 293-4 Pantone.

*Young foliage, under side, marginal tint*.—Near S 158-6 Pantone.

*Mature foliage, upper side, near apex*.—Near S 323-1 Pantone.

*Mature foliage, upper side, near base*.—Near S 134-7 Pantone.

*Mature foliage, under side, near apex*.—Near S 323-1 Pantone.

*Mature foliage, under side, near base*.—Near S 134-7 Pantone.

Venation: There is no visual appearance of venation. Indistinguishable from leaf blade.

FLOWER

Natural flowering season: March and April.

Inflorescence type and habit: Erect, lax, flat-topped panicle.

Rate of flower opening: 1 flower opens every 2-3 days.

Flower longevity on plant: 3-5 days, depending upon ambient temperatures.

Quantity of flowers: 98.

*Total inflorescence size*.—Height: Approximately 24 cm. Width: Approximately 11 cm.

Corolla:

*Arrangement*.—4-merous.

*Size*.—Length: Approximately 1.3 cm. Width: Approximately 1.5 cm at widest point. Lobe Length: Approximately 1.2 cm. Lobe width: Approximately 1.4 cm.

Petals:

*Margin*.—Entire.

*Shape*.—Campanulate.

*Apex*.—Acute.

*Texture*.—Glabrous.

Color: The outer surface of petal is often divided longitudinally into lobes of two colors; a pink color and an apricot color.

*When opening*.—Petal color, outer surface, apricot color of petal: Near S 90-7. Petal color, outer surface, pink color of petal: Near S 129-4. Inner surface not visible until fully opened.

*Fully opened*.—Outer surface: Near S 142-4 for one half of petal; near S 125-5 for other half of petal. Inner surface: Near S 148-6. Color Changes when Aging: Near S 97-9.

Bud: (near opening):

*Shape*.—Cylindrical.

*Length*.—Approximately 0.7 cm.

*Diameter*.—Approximately 0.3 cm.

*Color*.—Near S 76-5 Pantone.

Sepals:

*Margin*.—Entire.

*Shape*.—Deltoid.

*Apex*.—Acute.

*Texture*.—Glabrous.

*Color*.—Outer: Near S 308-5 Pantone with green striations of S 106 Pantone, resulting in the appearance of S 103-4 Pantone. Inner: Near S 308-4 Pantone.

*Pedicels*.—Length: Approximately 0.1 cm. Width: Approximately 0.1 cm. Strength: Strong. Texture: Glabrous. Color: Near S 85-3 Pantone.

*Fragrance*.—None detected.

REPRODUCTIVE ORGANS

Stamens: (Androecium).

*Number*.—Average 8.

*Filament length*.—Approximately 0.4 cm.

*Filament color*.—Near S 310-6.

*Anther length*.—0.1 cm.

*Anther color*.—Near S 312-5 Pantone.

*Anther shape*.—Ovate-oblong.

*Pollen color*.—Near S 18-5 Pantone.

Pistil: (Gynoecium).

*Number*.—Average 4.

*Length*.—Approximately 1.3 cm.

*Style color*.—Near S 304-4 Pantone.

*Stigma*.—Shape: Rounded. Color: Near S 49-7 Pantone. Ovary Color: Near S 295-3 Pantone.

OTHER CHARACTERISTICS

Fruits and seeds: Typical to Genus. Minute, approximately 1 mm dry seeds. Colored brown, too small to accurately measure with color chart.

Temperature tolerance: Tolerates temperatures from approximately 0° C. to at least 32° C.

Disease/pest resistance: Some resistance to powdery mildew. Neither resistance or susceptibility to other normal diseases and pests of *Kalanchoe* has been observed.

Drought tolerance: Tolerates at least 3 weeks of high temperatures without supplemental water, showing no serious damage to plant.

What is claimed is:

1. A new and distinct cultivar of *Kalanchoe* plant named 'BORDEAUX' as herein illustrated and described.

* * * * *